US010905357B2

(12) United States Patent
Friberg et al.

(10) Patent No.: US 10,905,357 B2
(45) Date of Patent: Feb. 2, 2021

(54) RESPIRATORY FLOW SENSOR

(71) Applicant: iAsset ag, Buchs (CH)

(72) Inventors: Harri Friberg, Mauren (LI); Jakob Daescher, Flasch (CH)

(73) Assignee: IMTMEDICAL AG, Buchs (CH)

( * ) Notice: Subject to any disclaimer, the term of this patent is extended or adjusted under 35 U.S.C. 154(b) by 234 days.

(21) Appl. No.: 15/859,425

(22) PCT Filed: Jul. 1, 2016

(86) PCT No.: PCT/IB2016/053977
§ 371 (c)(1),
(2) Date: Dec. 30, 2017

(87) PCT Pub. No.: WO2017/002091
PCT Pub. Date: Jan. 5, 2017

(65) Prior Publication Data
US 2018/0242883 A1 Aug. 30, 2018

(30) Foreign Application Priority Data
Jul. 1, 2015 (EP) ..................... 15174891

(51) Int. Cl.
A61B 5/087 (2006.01)
G01F 1/36 (2006.01)
G01F 1/42 (2006.01)
A61M 16/00 (2006.01)
(52) U.S. Cl.
CPC ....... *A61B 5/0876* (2013.01); *A61M 16/0003* (2014.02); *G01F 1/363* (2013.01); *G01F 1/42* (2013.01); *A61M 2016/0036* (2013.01)

(58) Field of Classification Search
CPC ..... A61B 5/0876; A61B 5/087; A61B 5/0871; A61B 5/0873; A61M 16/0003; A61M 2016/0036; G01F 1/42; G01F 1/363
USPC ........................................................ 600/538
See application file for complete search history.

(56) References Cited

U.S. PATENT DOCUMENTS

2007/0131279 A1  6/2007  Thakre et al.
2015/0283351 A1* 10/2015  Castello ............. A61M 16/021
                                                          600/538

FOREIGN PATENT DOCUMENTS

DE      4034176 A1      11/1991
EP      0331773 A1 *    9/1989  ............. G01F 1/40
EP      2275783 A2      1/2011
JP      2006105284 A *  4/2006
(Continued)

*Primary Examiner* — Jacqueline Cheng
*Assistant Examiner* — Tho Q Tran
(74) *Attorney, Agent, or Firm* — Nadya Reingand; Yan Hankin

(57) ABSTRACT

The invention relates to a respiratory flow sensor (11) comprising a flow tube (12) which has a flow channel (13) and tube connections for tubes at the free ends (15, 17) of the flow tube, a cover flap (32) which is arranged in the flow channel (13) and divides the flow channel (13) into a first flow channel section (18) and a second flow channel section (19), and comprising connections (22, 23) which open into the flow channel (13) on both sides of the cover flap (32) and which are used to decrease the pressure difference generated by the cover flap (32). A drainage device (41) which comprises drain grooves (42, 43) is provided in the flow channel (13), and the cover flap (32) has a hinge region which is formed by a first slot and a second H-shaped slot.

12 Claims, 5 Drawing Sheets

(56) References Cited

FOREIGN PATENT DOCUMENTS

KR          101508854 B1  *  4/2015
WO     WO-2012000101 A1  *  1/2012   ........... A61B 5/0876

* cited by examiner

RESPIRATORY FLOW SENSOR

CROSS-REFERENCE TO RELATED APPLICATION

This application is a 35 U.S.C. 371 national-phase entry of PCT International application no. PCT/IB2016/053977 filed on Jul. 1, 2016, which claims benefit of priority to prior European application no. 15174891.0 filed on Jul. 1, 2015, both of which are incorporated herein by reference in their entireties for all intents and purposes, as if identically set forth in fill herein.

FIELD OF INVENTION

The invention relates to a respiratory flow sensor according to the preamble of claim 1 or 9.

BACKGROUND OF THE INVENTION

Respiratory flow sensors, also referred to as differential pressure flow sensors, flow measuring sensors or flow sensors, are arranged between a tube, which comes from a respiratory or anesthetic device, and a tube, which is supplied to the patient.

A respiratory flow sensor comprising a flow pipe, comprising a cover flap and comprising connections, is known from U.S. Pat. No. 5,979,247A. The flow pipe has a cylindrical flow channel and, on the free ends thereof, hose connections for the hoses. The cover flap is arranged in the flow channel and divides the flow channel into a first flow channel section and into a second flow channel section. The cover flap further has a hinge region and a free end region located opposite the hinge region. The hinge region is formed by a first slot and by a second slot, wherein the second slot is arranged between the first slot. On both sides of the cover flap, the connections lead into the flow channel and serve for the reduction of the differential pressure created by the cover flap.

If air or the breath, respectively, of the patient forms the respiratory flow sensor, the deflectable cover flap forms a flow resistance. For a reliable use, a respiratory flow sensor needs to have a sufficient measurement accuracy. High differential pressures appear in the respiratory flow sensor, in particular in the case of a respiratory flow sensor for children, which has a relatively small diameter of the flow channel. Even small influences thus have a large effect on the result of a measurement, which is carried out.

The breathing air of the patient also includes moisture, which deposits as liquid in the flow channel of the respiratory flow sensor during the respiration. This liquid can lead to a measurement noise on the useful signal and can thus cause an inaccurate measurement. The liquid located in the respiratory flow sensor can also have the effect that the result of this measurement is greatly distorted, because the characteristic of the cover flap changes as a result of an liquid application. As a result of a high liquid level in the flow channel, the mobility or the deflectability of the cover flap can further be greatly impacted. These effects appear in particular when the liquid collects in a region of the flow channel, in which the cover flap is arranged.

It has now already been proposed to arrange the respiratory flow sensor between the hoses in such a way in each case that said respiratory flow sensor comes to rest in an inclined orientation and that the liquid, which is located in the respiratory flow sensor due to the force of gravity, can drain. However, the patient often moves during the duration of a respiration process or during an anesthesia. The respiratory flow sensor, which is arranged at an incline, might thus come into a position, in which a water drainage of the respiratory flow sensor does not take place any longer and a sufficient measurement accuracy is thus no longer ensured.

In the case of a respiratory flow sensor, it is known from US200701313279A1 to provide drainage pipes, which can in each case be closed by means of a valve and which protrudes perpendicularly to the outside, on both sides of a stationary flow resistance.

The construction of this type of water drainage is extensive and leads to correspondingly high production costs for the respiratory flow sensor. Such respiratory flow sensors, however, are often disposable parts, so that the production costs are to be kept as low as possible.

Due to the hinge region of the cover flap, which comprises to joint regions or hinges, respectively, which are spaced apart from one another, the cover flap according to U.S. Pat. No. 5,979,247A is subjected to torsional stresses only to a limited extent, in particular in the case of high respiratory flows. After a certain period of use, however, breakages, which can also lead to inaccurate measurement results, occur again and again in this hinge region.

A respiratory flow sensor comprising a flow pipe, comprising a cover flap and comprising connections, is known from DE19617738C1. The flow pipe has a flow channel, which has a rectangular cross section and, on the free end thereof, has hose connections for hoses. The cover flap is arranged into the flow channel and divides the flow channel into a first flow channel section and into a second flow channel section. The cover flap further has a hinge region and a free end region located opposite the hinge region. The hinge region is formed by a first slot and by a second slot, wherein the second slot is arranged between the first slot. On both sides of the cover flap, the connections lead into the flow channel and serve for the reduction of the differential pressure created by the cover flap.

In the case of a respiratory flow sensor according to DE19617738C1, liquid can also collect in the flow channel and breakages occur again and again in the hinge region of the cover flap after a certain period of use.

A respiratory flow sensor is known from U.S. Pat. No. 4,989,456A, which has a flow pipe, which has a flow channel and, on the free ends thereof, hose connections for hoses, a cover flap, which is arranged in the flow channel and which divides the flow channel into a first flow channel section and into a second flow channel section, and has connections, which lead into the flow channel on both sides of the cover flap and serve for the reduction of the differential pressure created by the cover flap. Provision is made in the flow channel for two annularly running accommodating chambers as water draining device of the respiratory flow sensor. Moisture, which accumulates in the respiratory flow sensor, is collected in these accommodating chambers.

It is a disadvantage of this known solution that the moisture, which accumulates during the entire measuring process, is still located in the respiratory flow sensor and distortions of the measurement results can also result caused by moisture depositions. Depending on the orientation of the respiratory flow sensor, liquid located in the accommodating chamber can also escape unintentionally.

The cover flap of U.S. Pat. No. 4,989,456A has hinges, which are formed by slots, which run in opposite directions. This embodiment prevents breakages in the hinge regions only to a limited extent during a longer period of use.

EP2275783A2 shows a respiratory flow sensor comprising a cover flap, the hinge region of which has a plurality of slots, which are arranged parallel to one another.

The disadvantage of this solution is that unwanted deflection movements of the cover flap can occur under pressure due to this embodiment of the hinge region in particular in the case of respiratory flow sensors with smaller dimensions, as they are used for the respiration and anesthesia of children. This can go so far that the cover flap starts to flutter. If the material thickness of the cover flap is reinforced in such a way that unwanted deflection movements of the cover flap are prevented for the most part, this makes the measurement per se more difficult.

SUMMARY

It is thus the object of the invention at hand to create a respiratory flow sensor, which does not have the above-mentioned disadvantages and which in particular ensures a sufficient measurement accuracy in response to a long period of use.

The object is solved by means of the features of the independent claims. Advantageous further developments are specified in the figures and in the dependent patent claims.

According to a first approach of the invention, a respiratory flow sensor has a flow pipe, which has a flow channel and, on the free ends thereof, hose connections for hoses, a cover flap, which is arranged in the flow channel and which divides the flow channel into a first flow channel section and into a second flow channel section, and connections, which lead into the flow channel on both sides of the cover flap and serve for the reduction of the differential pressure created by the cover flap, wherein provision is made in the flow channel for a water drainage device, which comprises at least one drainage groove.

Moisture, which accumulates in the flow channel, drains in the at least one drainage groove for example and/or said moisture can collect in the at least one drainage groove. As an alternative or in addition to a drainage of the liquid, the maximum level of the liquid in the respiratory flow sensor is limited in the flow channel by this type of water drainage device. The water drainage device in the flow channel, which comprises at least one drainage groove, thus ensures that the liquid, which is located in the respiratory flow sensor, does not impact the deflection or the movement, respectively, of the cover flap, and that the liquid, which is located in the respiratory flow sensor, thus does not lead to distorted measurement results.

Advantageously, the at least one drainage groove extends in the flow-through direction of the respiratory flow sensor or the flow channel thereof, respectively, whereby a cumulative accumulation of liquid in the respiratory flow sensor and in particular in the region of the cover flap, is prevented in a preferred manner.

Advantageously, the at least one drainage groove is embodied in a channel-shaped manner and has for example a rectangular, U-shaped and/or V-shaped cross section.

The water drainage device preferably comprises a plurality of drainage grooves, so that the wall of the flow channel is not weakened excessively in the region of the drainage grooves in spite of the provision of a sufficiently large volume for accommodating liquid.

Advantageously, the drainage grooves are arranged so as to be spaced apart from one another in the circumferential direction, so that they are optimally arranged for a collection or drainage, respectively, or discharge of the liquid. In response to a rotation of the respiratory flow sensor about its flow-through axis, at least one drainage groove is thus also present for the collection or for the discharge, respectively, of the liquid.

The plurality of drainage grooves are preferably arranged along a region of the inner circumference of the flow channel, which extends maximally across half of the entire inner circumference of the flow channel. Based on the cross section of the flow channel, the region comprising the drainage grooves extends across maximally 180° of a full circle with 360°. With this arrangement of the plurality of drainage grooves, at least one drainage groove for the collection or for the discharge, respectively, of the liquid is always present in response to a rotation of the respiratory flow sensor about its flow-through axis in the common application.

The distances of the plurality of drainage grooves relative to one another are preferably different along the region of the inner circumference, which provides for an advantageous collection or discharge, respectively, of the liquid in the respiratory flow sensor.

Advantageously, the angular range of the outermost drainage grooves to the drainage grooves adjacent thereto, is larger than from the inner drainage grooves relative to one another. During the respiration or during the anesthesia, respectively, the respiratory flow sensor typically rotates about the flow-through axis only across a small angular range. As a result of the arrangement of the inner drainage grooves closer to one another, a sufficiently large volume for accommodating or draining, respectively, the liquid is available in the case of a common application of the respiratory flow sensor and based on the force of gravity.

Starting at the closure cap, the at least one drainage groove preferably runs in a direction of the corresponding free end of the flow pipe along a curved line, so that an advantageous drainage or discharge of the liquid is at hand due to the force of gravity. Starting at the closure cap, in the alternative, the at least one drainage groove runs in a direction of the corresponding free end of the flow pipe along an inclined surface, which is arranged at an angle to the flow-through axis of the flow channel.

In the region of the water drainage device, at least one flow channel section preferably runs in a curved manner, so that an advantageous drainage or discharge of the liquid is at hand by means of the force of gravity.

Starting at the cover flap, the cross section of at least one flow channel section in the region of the water drainage device preferably increases in a direction of the corresponding free end of the flow pipe, so that a drainage or discharge of the liquid is at hand by means of the force of gravity. Advantageously, the flow channel section increases across its entire circumference, so that the relative position of the respiratory flow sensor with regard to the flow-through axis of the flow channel has no impact.

The increasing flow channel section is preferably embodied in a trumpet-shaped manner, which provides for a simple production with simultaneously advantageous drainage or discharge of the liquid. In the alternative, the increasing flow channel section is embodied conically.

According to a further advantageous approach, a respiratory flow sensor has a flow pipe, which has a flow channel and, on the free ends thereof, hose connections for hoses, a cover flap, which is arranged in the flow channel and which divides the flow channel into a first flow channel section and into a second flow channel section, wherein the cover flap has a hinge region and a free end region located opposite the hinge region, and connections, which lead into the flow channel on both sides of the cover flap and serve for the reduction of the differential pressure created by the cover flap, wherein provision is made in the flow channel for at least one stop section for the free end region of the cover flap for the limitation of the deflection of the cover flap.

The at least one stop section limits the maximum deflection of the cover flap, whereby the latter and thus the respiratory flow sensor is more suitable for use as compared to the solutions known from the relevant prior art.

In the case of the stop section, provision is advantageously made in the case of the stop section for a water drainage device for the liquid, which accumulates in the respiratory flow sensor, e.g. in the form of at least one drainage groove or a collection tank.

Provision is further preferably made in the flow channel for two stop sections located opposite one another, for defining the deflection of the cover flap in both directions, whereby the suitability for use of the respiratory flow sensor is improved additionally, because the cover flap can pivot only across the region, which is defined by the distance of the stop sections relative to one another.

Provision is advantageously made between the two stop sections for a water drainage device for the liquid, which accumulates in the respiratory flow sensor, e.g. in the form of a collection tank.

According to a further approach of the invention, a respiratory flow sensor has a flow pipe, which has a flow channel and, on the free ends thereof, hose connections for hoses, a cover flap, which is arranged in the flow channel and which divides the flow channel into a first flow channel section and into a second flow channel section, wherein the cover flap has a hinge region, which is formed by a first slot and at least a second slot, and connections, which lead into the flow channel on both sides of the cover flap and serve for the reduction of the differential pressure created by the cover flap, wherein the at least one second slot of the hinge region of the cover flap is embodied in an H-shaped manner and provision is in each case made adjacent to the at least one second slot for one lateral slot each.

This embodiment of the slots does not only prevent a torsional movement of the cover flap in response to high respiratory flows, but ensures a high safety against a rupturing of the cover flap in the hinge region thereof. With a high measurement accuracy, this respiratory flow sensor according to the invention thus has a long suitability for use. The cover flap advantageously has a polygonal and/or axially symmetrical cross section.

The ends of at least the at least one second slot preferably have inclined surfaces or radii, whereby stress peaks in response to the deflection of the cover flap in these regions of the slots is reduced and the suitability for use of the cover flap and thus of the entire respiratory flow sensor is improved. Advantageously, all ends of the slots in the cover flap are provided with inclined surfaces or radii.

Further advantages, features and details of the invention follow from the description below, in which exemplary embodiments of the invention are described with reference to the drawings.

BRIEF DESCRIPTION OF THE DRAWINGS

The list of reference numerals as well as the technical content of the patent claims and figures is part of the disclosure. The figures are described cohesively and comprehensively. Identical reference numerals mean identical components, reference numerals with different indices specify functionally identical or similar components.

DETAILED DESCRIPTION OF THE PREFERRED EMBODIMENT

Figure 1:
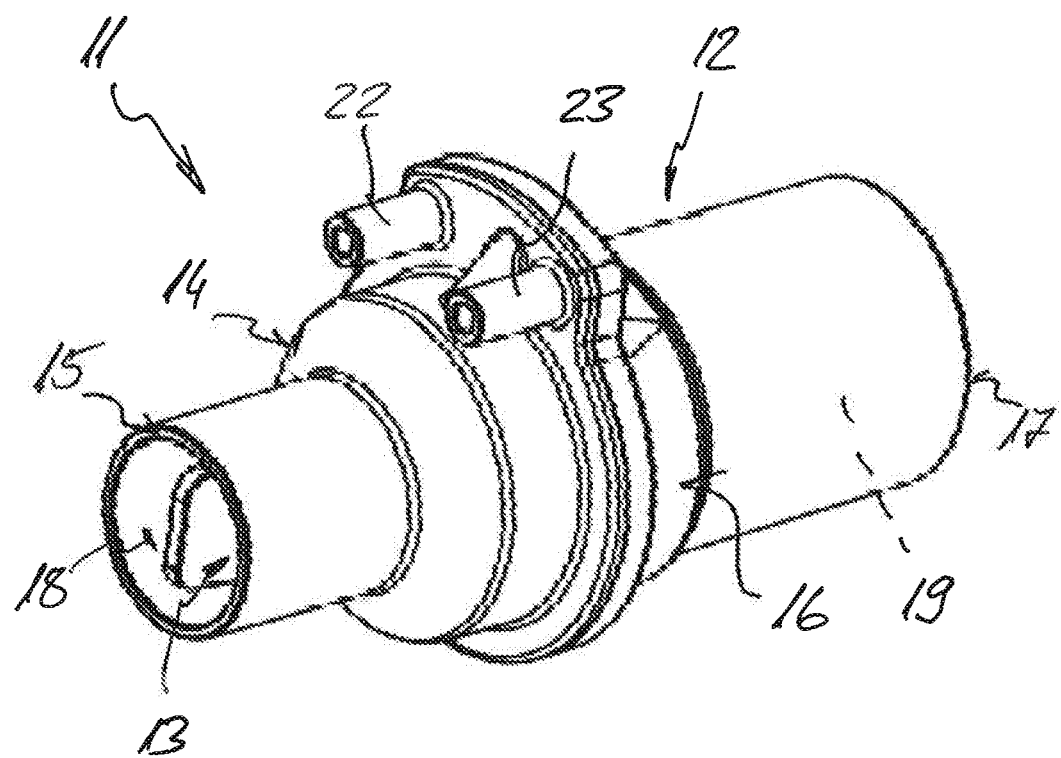
FIG. 1 shows a respiratory flow sensor according to the invention in a perspective view.
Figure 2:
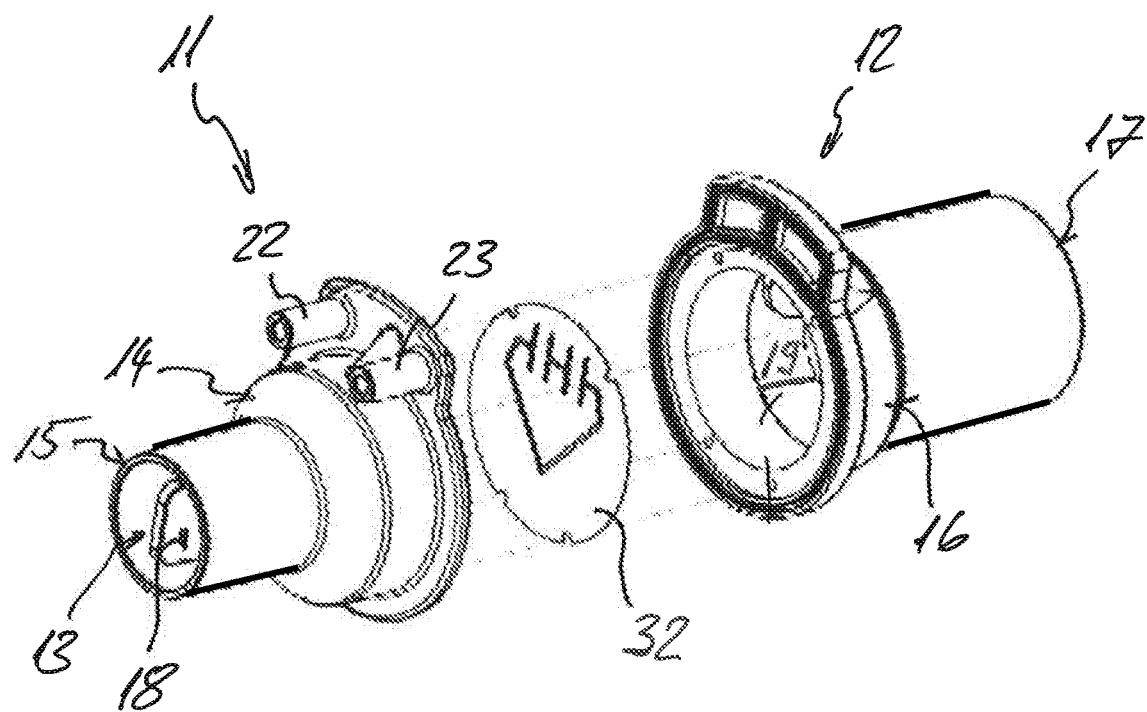
FIG. 2 shows the respiratory flow sensor according to FIG. 1 in an exploded illustration.
Figure 3:
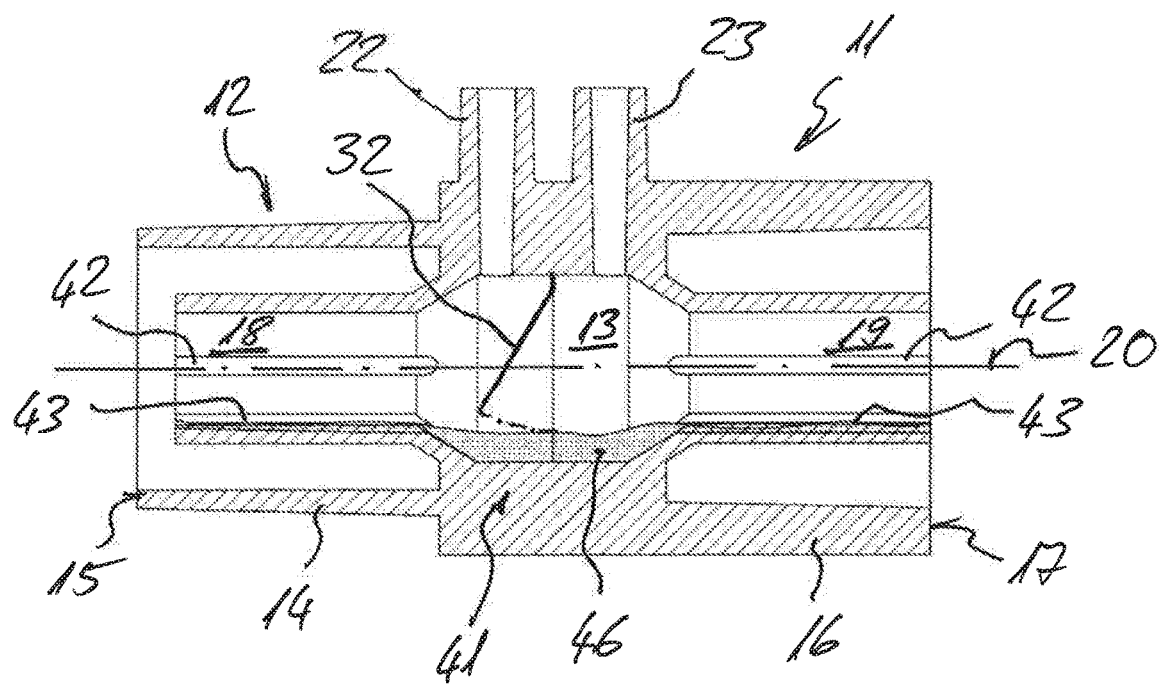
FIG. 3 shows a schematic longitudinal section through a respiratory flow sensor according to the invention, FIG. 4A-D in each case shows the respiratory flow sensor according to FIG. 3 in cross section.

The respiratory flow sensor 11 illustrated in FIGS. 1 and 2 has a flow pipe 12, a cover flap 32 and connections 22 and 23. The cylindrical flow pipe 12 has a flow channel 13 and, on the free ends 15 or 17 thereof, respectively, hose connections for hoses.

The flow pipe 12 is embodied in two parts (flow pipe section 14 and flow pipe section 16), wherein the cover flap 32 is arranged in the flow channel 13 between the flow pipe sections 14 and 16. The cover flap 32 divides the flow channel 13 into a first flow channel section 18 and into a second flow channel section 19. In the region, in which the cover flap 32 comes to rest in the joined state of the flow pipe sections 14 and 16, the flow pipe sections 14 and 16 in each case have a larger flow-through cross section.

The connection 22 leads into the flow channel 13 in the first flow channel section 18 and the connection 23 leads into the flow channel 13 in the second flow channel section 19. The connections 22 and 23 thus lead into the flow channel 13 on both sides of the cover flap 32 and serve for the reduction of the differential pressure created by the cover flap 32.

A water drainage device 41 is provided in the flow channel 13.

In the illustration, which is simplified schematically in FIGS. 3 and 4A to 4D, the water drainage device 41 comprises a plurality of drainage grooves 42 or 43, respectively, which are arranged circumferentially spaced apart from one another. The liquid 46, which accumulates in the respiratory flow sensor 11, is collected in the drainage grooves 42 and 43 and is drained into it, if applicable. The drainage grooves 42 and 43 are embodied in such a way that the movement of the cover flap 32 is not impacted by them.

Figures 4A, 4B:
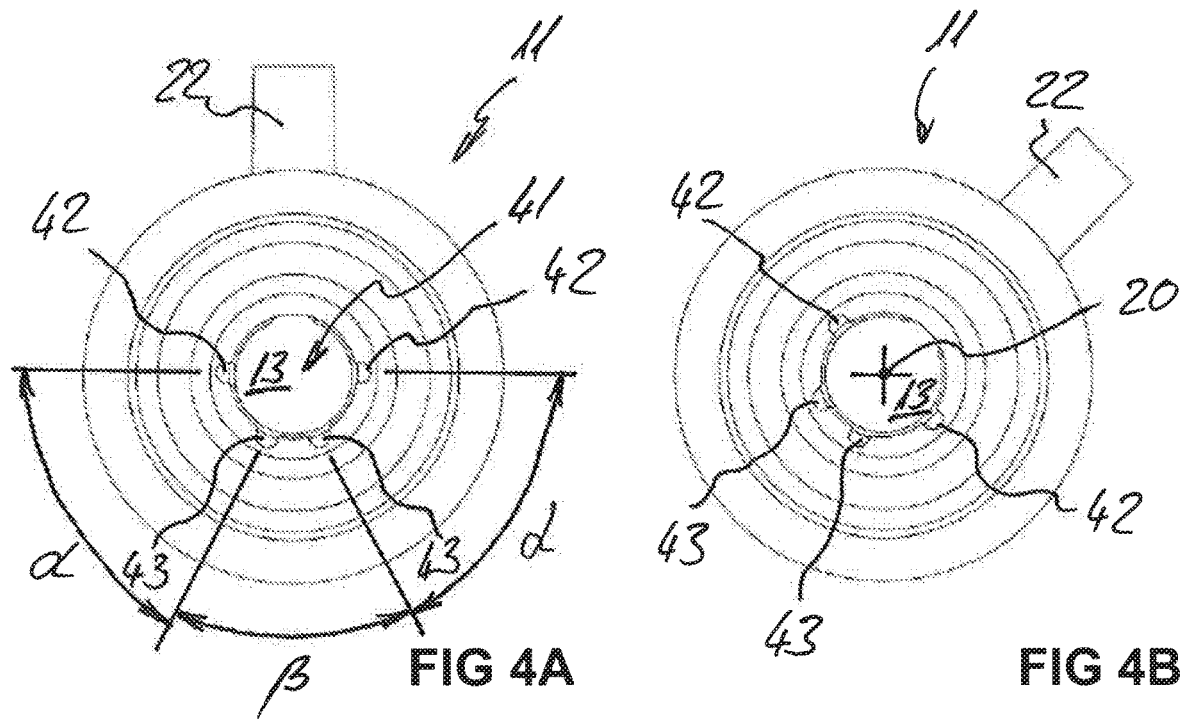
Figure 4C:
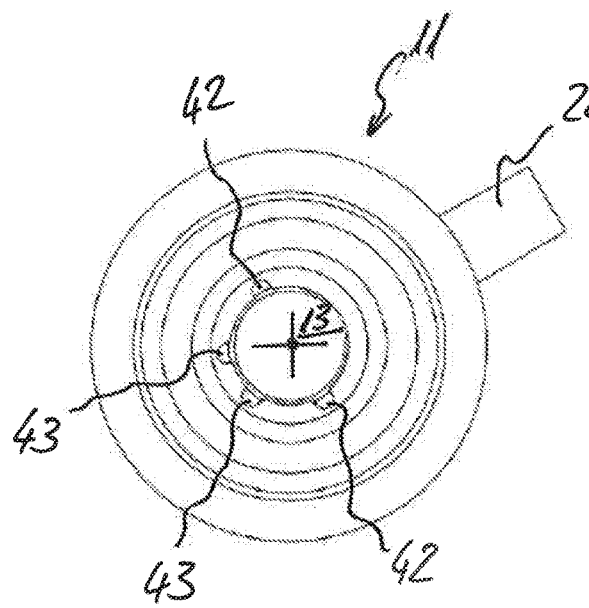
Figure 4D:
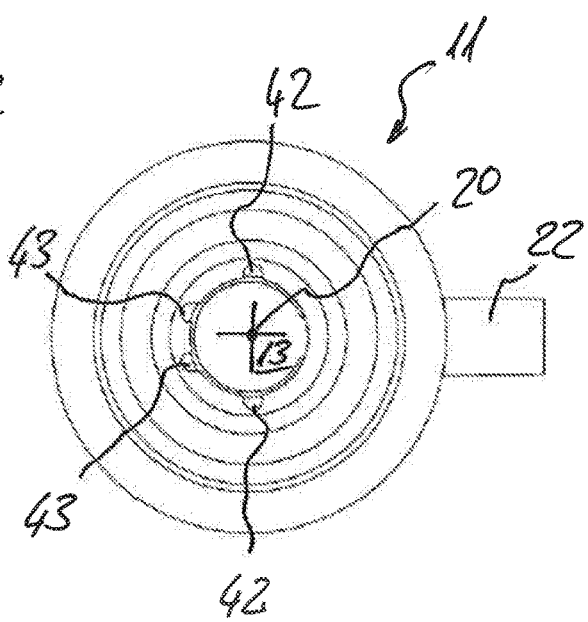

The drainage grooves 42 and 43 are arranged along a region of the inner circumference of the flow channel 13, which extends across half of the entire inner circumference of the flow channel 13 (see FIG. 4A; $2 \times \alpha + \beta$). The distance (angular dimension $\alpha$) of the drainage grooves 42 to the drainage grooves 43 is larger than the distance (angular dimension $\beta$) of the drainage grooves 43 to one another. Such an arrangement of the drainage grooves 42 and 43 ensures that a sufficient measurement accuracy with the respiratory flow sensor 11 is also ensured by means of the water drainage device 41, when said respiratory flow sensor is rotated about its flow-through axis 20 area by area (see FIGS. 4A to 4D). The flow-through axis 20 corresponds to the center axis of the flow channel 13.

Starting at the cover flap 32, individual or all drainage grooves 42 and/or 43 can run along a curved line in a direction of the corresponding free end 15 or 17, respectively, of the flow pipe 12. Starting at the cover flap 32, individual or all drainage grooves 42 and/or 43 can, in the alternative, run in a direction of the corresponding free end 15 or 17, respectively, of the flow pipe 12 along an inclined surface, which is arranged at an angle to the flow-through axis 20 of the flow channel 13.

Figure 5:
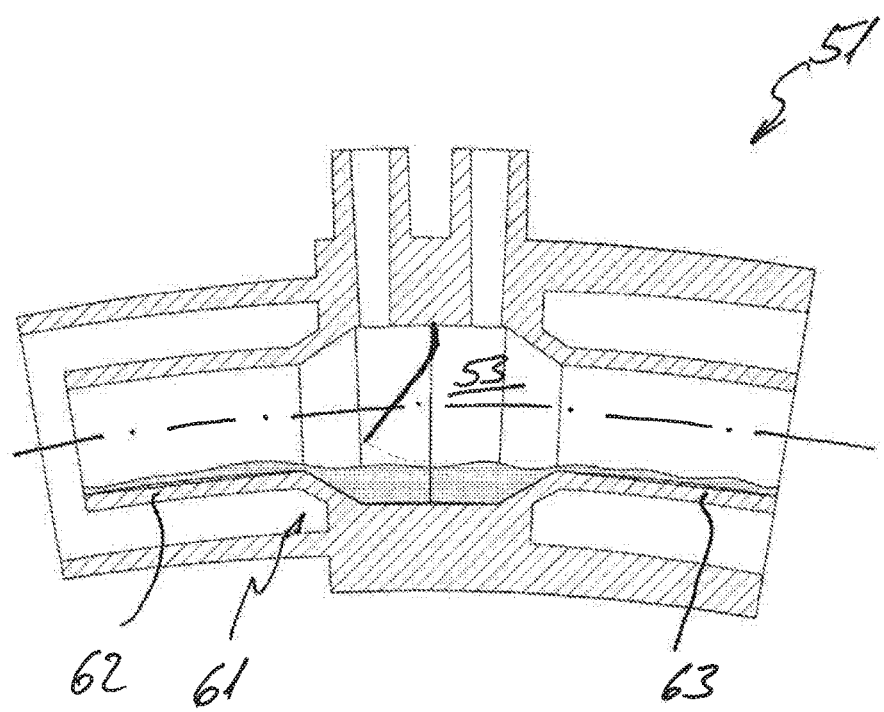
FIG. 5 shows a schematic longitudinal section though an alternative according to the invention of the respiratory flow sensor according to FIG. 3.

In the case of the exemplary embodiment, which is illustrated in a schematically simplified manner in FIG. 5, the flow channel sections 62 and 63 in each case run in a curved manner in the region of the water drainage device 61 of the respiratory flow sensor 51. In the case of this exemplary embodiment, the flow channel 53 also runs in a curved manner.

Figure 6:
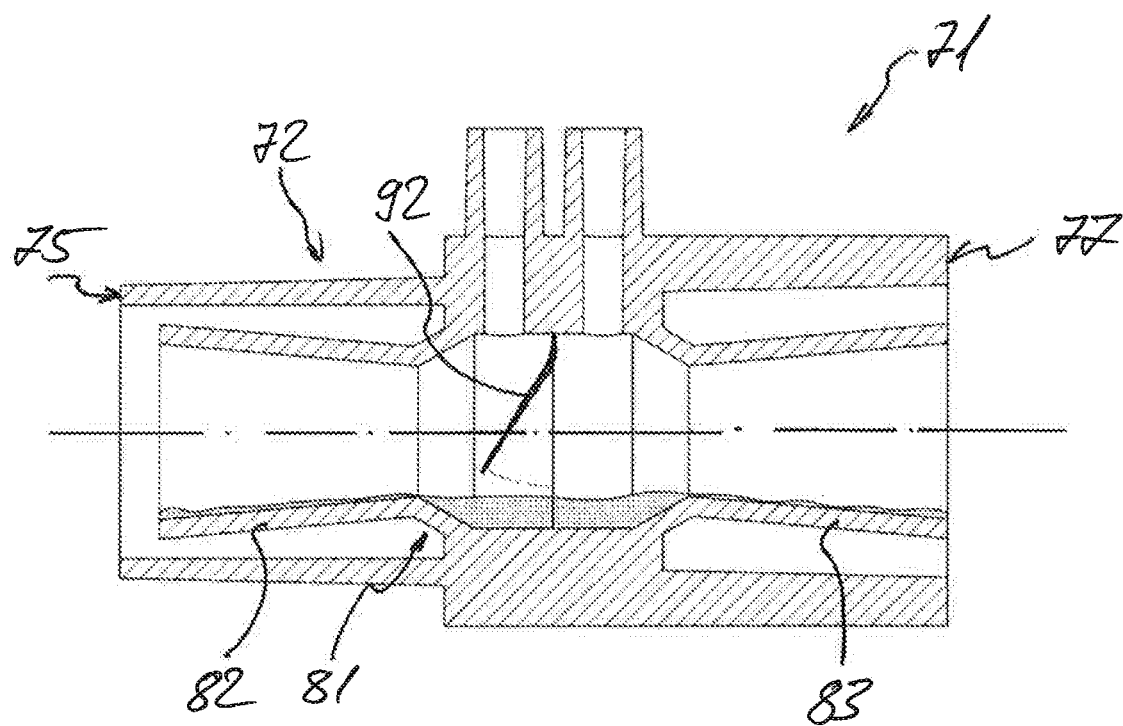
FIG. 6 shows a schematic longitudinal section through a further alternative according to the invention of the respiratory flow sensor according to FIG. 3.

In the exemplary embodiment, which is illustrated in a schematically simplified manner in FIG. 6, the cross sections of the flow channel sections 82 and 83 increase in the region of the water drainage device 81 of the respiratory low sensor 71, starting at the cover flap 92 in a direction of the corresponding free end 75 or 77, respectively, of the flow pipe 72. The flow channel sections 82 or 83, respectively, are in each case embodied conically. In the alternative, at least one of the flow channel sections 82 or 83 could also be embodied in a trumpet-shaped manner.

Figure 7:
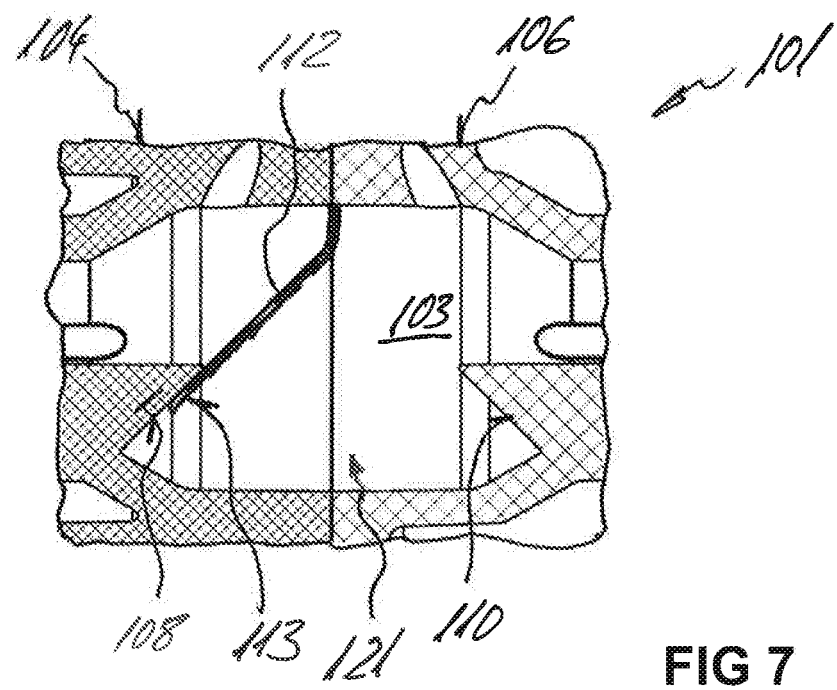
FIG. 7 shows a respiratory flow sensor in a detailed section.

In the flow pipe section 104, the respiratory flow sensor 101 shown only in sections in FIG. 7 has a stop section 108 and, in the flow pipe section 106 a stop section 110, against which the free end region 113 of the cover flap 112 can come to rest. The stop sections 108 and 110 in the flow channel 103, which are located opposite one another, define the maximum deflection of the cover flap 112 in both directions. The suitability for use of the respiratory flow sensor is thus improved additionally, because the cover flap can pivot only across the region, which is defined by the distance of the stop sections relative to one another.

Provision is made between the stop sections 108 and 110 for a water drainage device 121, which is embodied in a trough-shaped manner to accommodate liquid. At least one such stop section can also be provided in the respiratory flow sensor 11, 51 or 71, wherein the drainage of the accumulating liquid is advantageously ensured for example by means of the arrangement of corresponding recesses or slots in the stop section.

Figure 8:
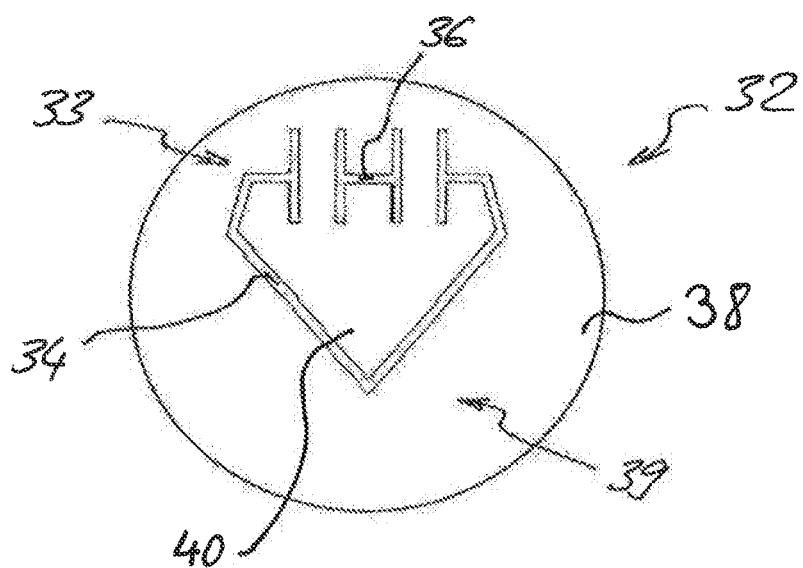
FIG. 8 shows the cover flap of a respiratory flow sensor according to the invention according to FIG. 1 in a view.
Figure 9:
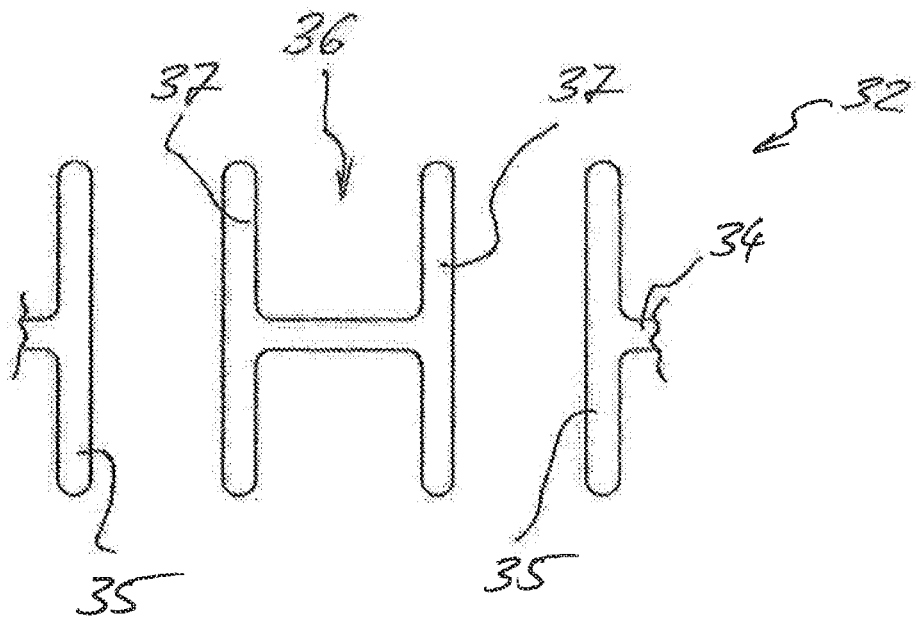
FIG. 9 shows the hinge of the cover flap according to FIG. 8 in a detailed view.

Here, the cover flap 32 illustrated in FIGS. 8 and 9 has a circular and disk-shaped base body comprising a section 38, which is fixed in the installed state, and a movable flap section 39. The flap section 39 is connected to the fixed section 38 via a hinge region 33 and is separated therefrom by means of a first slot 34. The flap section 39 has a free end region 40, which is located opposite the hinge region 33. The hinge region 33 is formed by the first slot 34 and a second slot 36. The second slot 36 is embodied in an H-shaped manner, wherein provision is in each case also made spaced apart in parallel to the flanges 37 of the second slot 36 for a lateral slot 35, into which the first slot 34 leads on both sides. All ends of the second slot 36 and of the lateral slots 35 have radii (see FIG. 9). In the alternative, these ends can also have inclined surfaces List of Reference Numerals 11 respiratory flow sensor
12 flow pipe
13 flow channel
14 flow pipe section
15 free end of 14
16 flow pipe section
17 free end of 16
18 1. flow channel section
19 2. flow channel section
20 flow-through axis
22 connection
23 connection
32 cover flap
33 hinge region
34 1. slot
35 lateral slot
36 2. slot
37 flange of 36
38 fixed section of 32
39 flap section of 32
40 free end region of 39
41 water drainage device
42 drainage groove
43 drainage groove
α angle between 42 and 43
β angle between 43 and 43
51 respiratory flow sensor
53 flow channel
61 water drainage device
62 flow channel section
63 flow channel section
71 respiratory flow sensor
72 flow pipe
75 free end
77 free end
81 water drainage device
82 flow channel section
83 flow channel section
92 cover flap
101 respiratory flow sensor
103 flow channel
104 flow pipe section
106 flow pipe section
108 stop section
110 stop section
112 cover flap
113 free end region of 112
121 water drainage device

What is claimed is:

1. A respiratory flow sensor, comprising:
 a flow pipe including a flow channel and first and second ends of the flow pipe;
 a cover flap, arranged in the flow channel, which divides the flow channel into a first flow channel section and a second flow channel section;
 first and second connections connected to the flow pipe, said first connection leading into said first flow channel section and said second connection leading into said second flow channel section, said first and second connections configured to reduce a pressure differential created by the cover flap during operation of the respiratory flow sensor; and
 a water drainage device in the flow channel, said water drainage device including at least one drainage groove.

2. The respiratory flow sensor according to claim 1, said water drainage device including a plurality of drainage grooves arranged, and spaced apart from one another, along a region of an inner circumference of the flow channel.

3. The respiratory flow sensor according to claim 2, wherein said region has a maximum extent no greater than half of the inner circumference of the flow channel.

4. The respiratory flow sensor according to claim 2, wherein said plurality of drainage grooves includes at least first, second, and third drainage grooves, and an angular distance, $\alpha$, between said first and second drainage grooves is different from an angular distance, $\beta$, between said second and third drainage grooves.

5. The respiratory flow sensor according to claim 1, wherein said at least one drainage groove extends from said cover flap toward one of said ends of said flow pipe along a curved line.

6. The respiratory flow sensor according to claim 1, wherein said at least one drainage groove extends from said cover flap toward one of said ends of said flow pipe along an inclined surface arranged at an angle to a flow-through axis of the flow channel.

7. The respiratory flow sensor according to claim 1, wherein at least one of said first and second flow channel sections runs in a curved manner in a region adjacent to said water drainage device.

8. The respiratory flow sensor according to claim 1, wherein a cross section of at least one of said first and second flow channel sections increases in a direction extending from said cover flap and toward a corresponding end of the flow pipe, in a region adjacent to said water drainage device.

9. The respiratory flow sensor according to claim 8, wherein said cross section is embodied conically.

10. The respiratory flow sensor according to claim 1, wherein said at least one drainage groove extends in a flow-through direction of said flow channel.

11. A respiratory flow sensor, comprising:
a flow pipe including a flow channel and first and second ends of the flow pipe;
a cover flap, arranged in the flow channel, which divides the flow channel into a first flow channel section and a second flow channel section, said cover flap including a hinge region that includes a first slot and at least one second slot, having an H-shape, and at least one lateral slot adjacent to the at least one second slot; and
first and second connections connected to the flow pipe, said first connection leading into said first flow channel section and said second connection leading into said second flow channel section, said first and second connections configured to reduce a pressure differential created by the cover flap during operation of the respiratory flow sensor.

12. The respiratory flow sensor of claim 11, wherein the ends of the at least one second slot have inclined surfaces or radii.

\* \* \* \* \*